(12) United States Patent
Kanemoto et al.

(10) Patent No.: US 10,232,166 B2
(45) Date of Patent: Mar. 19, 2019

(54) DEFIBRILLATION PAD

(71) Applicant: NIHON KOHDEN CORPORATION, Shinjuku-ku, Tokyo (JP)

(72) Inventors: Michio Kanemoto, Tokyo (JP); Shigehiro Nishiwaki, Tokyo (JP); Ryugo Odaka, Tokyo (JP); Takeshi Akiyama, Tokyo (JP); Yuya Komeiji, Tokyo (JP); Eishi Harasawa, Tokyo (JP)

(73) Assignee: NIHON KOHDEN CORPORATION, Tokyo (JP)

( * ) Notice: Subject to any disclaimer, the term of this patent is extended or adjusted under 35 U.S.C. 154(b) by 0 days.

(21) Appl. No.: 15/517,204

(22) PCT Filed: Dec. 4, 2015

(86) PCT No.: PCT/JP2015/006049
§ 371 (c)(1),
(2) Date: Apr. 6, 2017

(87) PCT Pub. No.: WO2016/092800
PCT Pub. Date: Jun. 16, 2016

(65) Prior Publication Data
US 2017/0296804 A1  Oct. 19, 2017

(30) Foreign Application Priority Data

Dec. 9, 2014 (JP) .................................. 2014-248584

(51) Int. Cl.
*A61N 1/04* (2006.01)
*A61N 1/39* (2006.01)
(Continued)

(52) U.S. Cl.
CPC ............ *A61N 1/046* (2013.01); *A61N 1/0492* (2013.01); *A61N 1/39* (2013.01); *A61N 1/3925* (2013.01);
(Continued)

(58) Field of Classification Search
CPC ......... A61N 1/046; A61N 1/39; A61N 1/0492
See application file for complete search history.

(56) References Cited

U.S. PATENT DOCUMENTS

| | | | | |
|---|---|---|---|---|
| 5,817,151 | A * | 10/1998 | Olson .................. | A61N 1/3931 607/142 |
| 2003/0055478 | A1 * | 3/2003 | Lyster .................... | A61N 1/046 607/142 |

(Continued)

FOREIGN PATENT DOCUMENTS

| | | |
|---|---|---|
| EP | 2 105 162 A2 | 9/2009 |
| JP | 2007-530125 A | 11/2007 |
| JP | 5113183 B2 | 1/2013 |
| WO | 2013-040214 A1 | 3/2013 |

OTHER PUBLICATIONS

Japanese Office action issued in Patent Application No. JP 2014-248584 dated Jan. 30, 2018.
International Search Report issued in Patent Application No. PCT/JP2015/006049 dated Mar. 15, 2016.
Written Opinion issued in Patent Application No. PCT/JP2015/006049 dated Mar. 15, 2016.

*Primary Examiner* — Amanda K Hulbert
*Assistant Examiner* — Natasha Patel
(74) *Attorney, Agent, or Firm* — Pearne & Gordon LLP

(57) ABSTRACT

A defibrillation pad for a defibrillator, includes: a pair of electrode pads (10) each including a gel portion (12); lead wires (21, 22); a pair of nonconductive release liners (30A, 30B) each detachably stuck to the corresponding gel portion (12) and each having a through hole (32A, 32B) opposed to (Continued)

the corresponding gel portion; and a connecting member (40) comprising an electric connecting pattern (41) having a predetermined electrical resistance, wherein the pair of gel portions (12), each of which is exposed from the corresponding through hole (32A, 32B), are electrically connected to each other through the electric connecting pattern (41) in a state where each of the pair of release liners (30A, 30B) are stuck to the corresponding gel portion. The connecting member (40) has a cut region (45) by which the pair of gel portions are electrically disconnected to each other when the pair of electrode pads are stuck to a living body.

14 Claims, 6 Drawing Sheets

(51) Int. Cl.
  *A61N 1/08* (2006.01)
  *A61N 1/372* (2006.01)

(52) U.S. Cl.
  CPC .................. *A61N 2001/083* (2013.01); *A61N 2001/37294* (2013.01)

(56) References Cited

U.S. PATENT DOCUMENTS

| | | | |
|---|---|---|---|
| 2003/0171797 A1* | 9/2003 | Nova | A61N 1/046 607/142 |
| 2007/0203558 A1 | 8/2007 | Jonsen et al. | |
| 2010/0094388 A1* | 4/2010 | Hauge | A61N 1/046 607/142 |
| 2010/0228332 A1 | 9/2010 | Hauge et al. | |
| 2011/0257695 A1 | 10/2011 | Jonsen et al. | |

* cited by examiner

[Fig. 1]
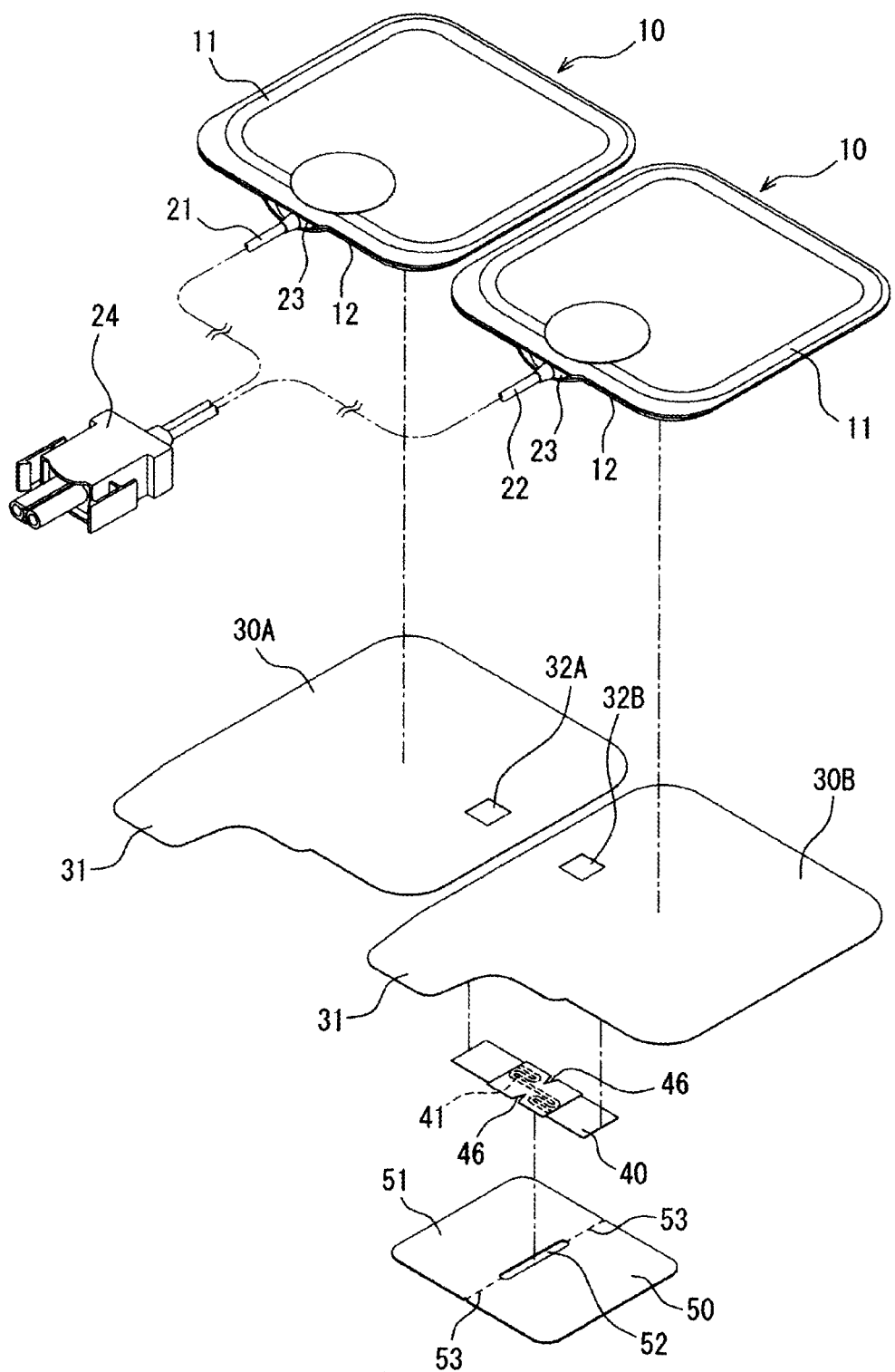

[Fig. 2]
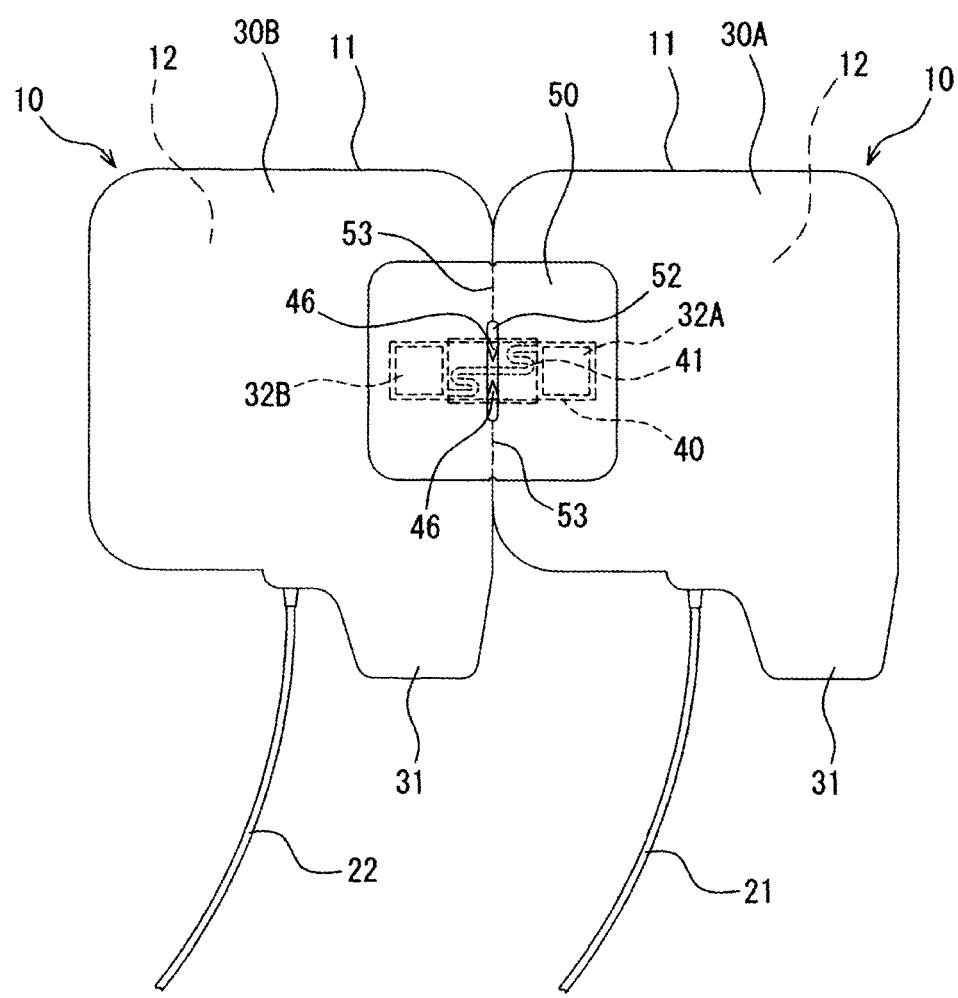

[Fig. 3]
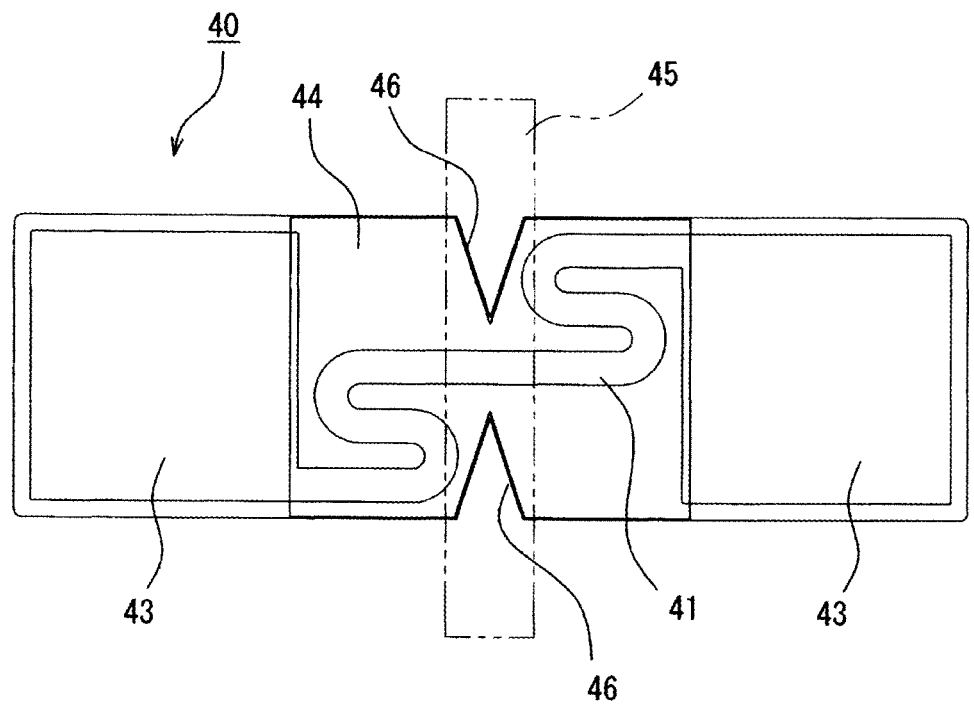
[Fig. 4]
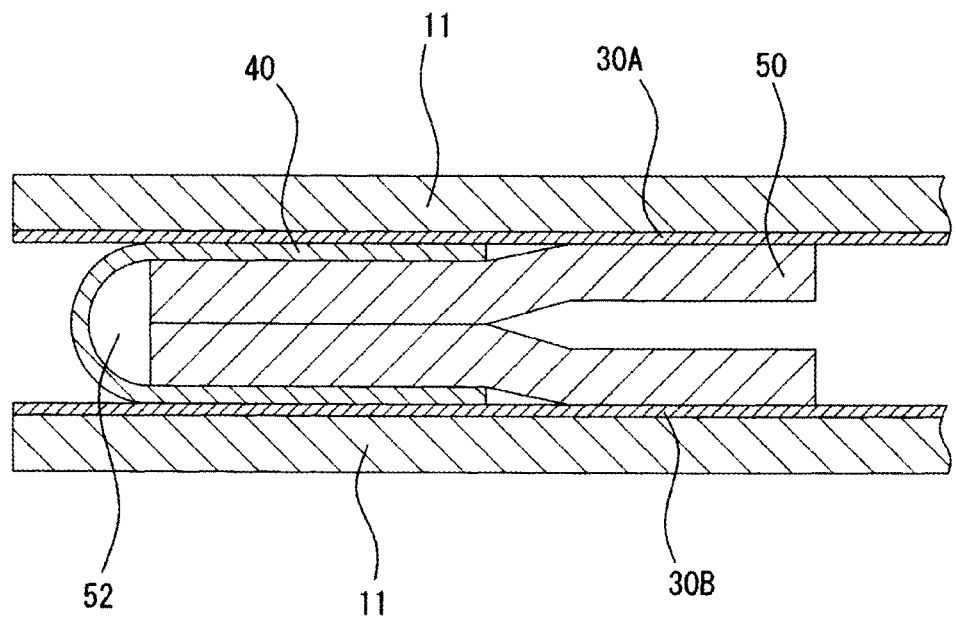

[Fig. 5]
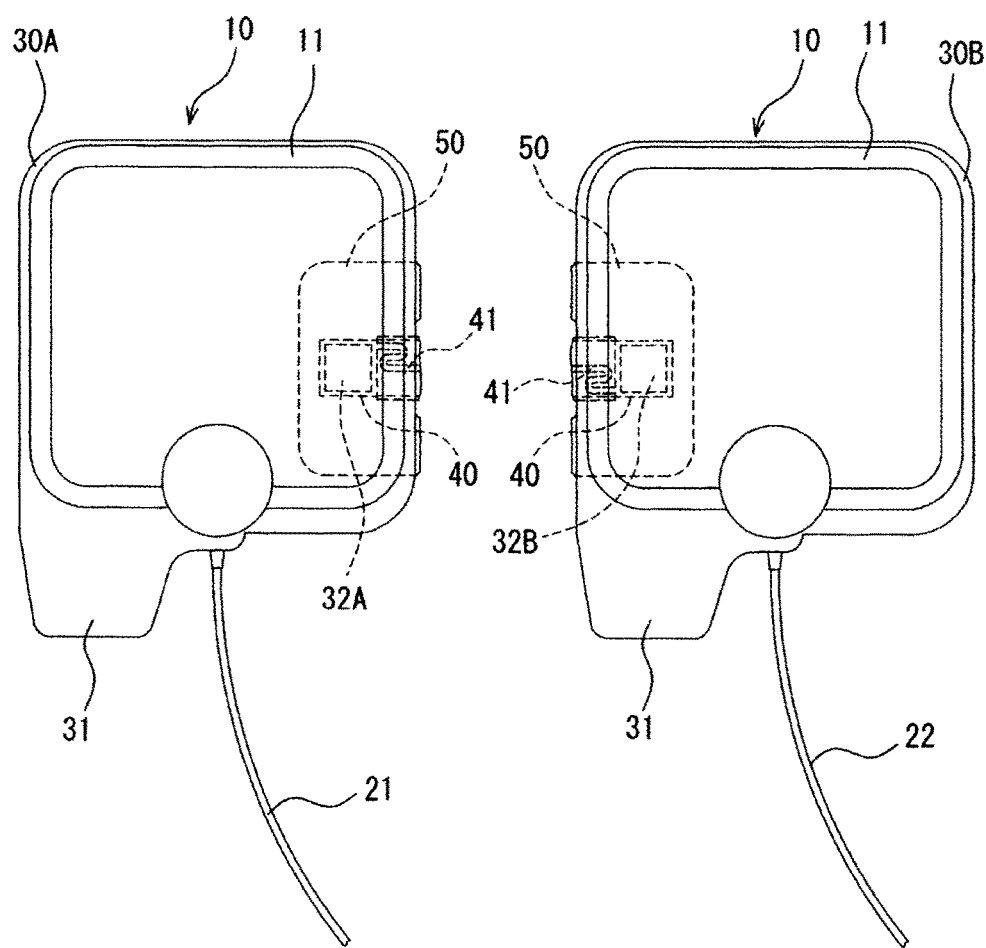

[Fig. 6]
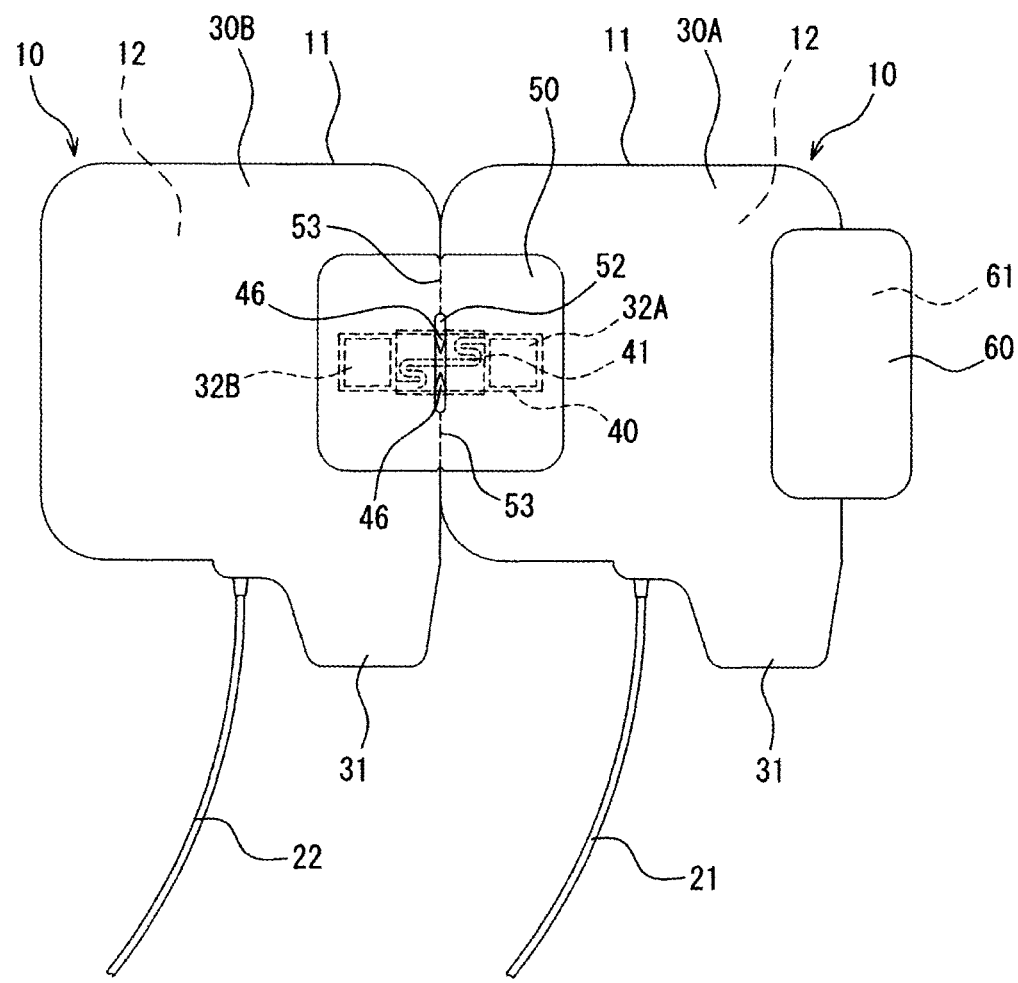
[Fig. 7]
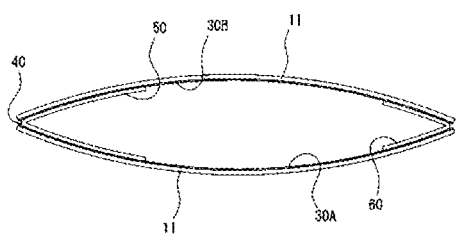

[Fig. 8]
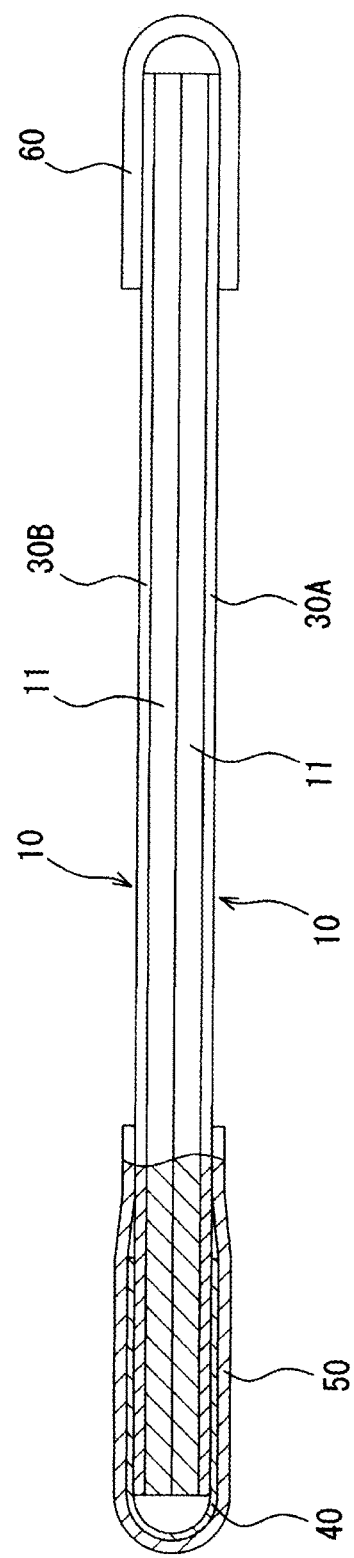

DEFIBRILLATION PAD

TECHNICAL FIELD

The present disclosure relates to a defibrillation pad for a defibrillator including a pair of electrode pads. Especially, the present disclosure relates to a defibrillation pad for an automated external defibrillator (AED), which is attached to the living body.

BACKGROUND

A pair of electrode pads are used in an AED. One ends of lead wires are connected to the electrode pads, respectively. The lead wires and the electrode pads are stored in a package while being housed in a hermetically sealed state. Parts of the lead wires extend from the interior of the package to the outside together with a connector to which the other ends of the lead wires are connected.

In the electrode pads, problems such as that, when the pads are to be used, necessary electrical conduction with the living body may not be attained and the pads may not be used must be avoided. In the case where electrode pads which have been once used (hereinafter, such electrode pads are sometimes referred to as used electrode pads) are again housed in a package in a state similar to the unused state, the pads must be in a condition where they can be recognized to be unusable. Also during storage (during standby), therefore, electrode pads are always connected to an AED, and periodically automatically checked by the AED, and, when an abnormality occurs, the AED informs of the abnormality. The checking process will be briefly described. A pair of electrode pads are housed in a package in a state where gel surfaces of the electrode pads are conductive with each other. The conduction state between the lead wires is monitored, thereby checking whether the connection between the lead wires is broken or not, and the drying degree of the gel.

A configuration is known where, in order to meet the request, for example, gel surfaces of paired electrode pads are stuck together in a state where the gel surfaces are opposed to each other through a punctured release liner to attain an electrical connection, and then the electrode pads are housed in a package (hereinafter, the configuration is referred to as Configuration example 1). Lead wires are connected to the electrode pads, respectively, and parts of the lead wires extend from the interior of the package to the outside together with a connector to which the opposite electrode pad side ends of the lead wires are connected. Therefore, a conduction test can be performed by causing a current to flow from the lead wires through the pair of electrode pads stored in the housed state.

JP5113183B2 discloses electrode pads in which a conduction test is performed by forming an electrically closed loop by: a release liner including two conductive sheets which are clamped between first and second nonconductive sheets; and a clip. In the first nonconductive sheet; a first hole which is connected to a gel of the first electrode pad, and a second hole which is not connected thereto are formed, and a first hole which is connected to a gel of the second electrode pad, and a second hole which is not connected thereto are formed. The second nonconductive sheet is a single sheet in which no hole is formed.

One of the conductive sheets is placed so as to connect between the first hole which is connected to the gel of the first electrode pad, and the second hole (on the side of the first electrode pad) which is not connected thereto. The other conductive sheet is placed so as to connect between the first hole which is connected to the gel of the second electrode pad, and the second hole (on the side of the second electrode pad) which is not connected thereto. According to the configuration, the gel of the first electrode pad is connected to the one conductive sheet through the first hole, and the one conductive sheet is located in the second hole on the side of the first electrode pad. The gel of the second electrode pad is connected to the other conductive sheet through the first hole, and the other conductive sheet is located in the second hole on the side of the second electrode pad. The one conductive sheet facing the second hole on the side of the first electrode pad, and the other conductive sheet facing the second hole on the side of the second electrode pad are connected to each other by the clip, whereby the electrical connection between the first and second electrode pads can be attained, and a conduction test can be performed by causing a current to flow from the lead wires connected respectively to the first and second electrode pads.

In the electrode pads of Configuration example 1, when the pads are to be used, it is possible to avoid problems (conduction breakage and the like) such as that electrical conduction with the living body is not attained and the pads cannot be used. When, after use, the pair of electrode pads are housed in a package while the gel surfaces are opposed to each other, however, electrical conduction is obtained regardless of whether a release liner is used or not, and therefore it is impossible to detect the state where the pads have been used.

In the electrode pads disclosed in JP511313B2, as described above, a conduction test can be performed in a stored state. Even when, after use, the electrode pads are returned to the original state through the release liner and housed in the package, electrical conduction cannot be obtained unless the clip is used, and therefore it is possible to detect the state where the pads have been used. When the electrode pads are housed in the package while the gel surfaces are opposed and directly stuck to each other, however, electrical conduction is obtained, and therefore it is impossible to detect the state where the pads have been used.

As described above, conventional electrode pads have a problem in that it is impossible to completely detect a situation where used electrode pads are housed in a package.

SUMMARY OF INVENTION

Illustrative aspects of the present invention provide a defibrillation pad in which a conduction test can be performed in a stored state, and a situation where used electrode pads are housed in a package can be detected.

According to an illustrative aspect of the present invention, there is provided a defibrillation pad for a defibrillator. The defibrillation pad comprises:
 a pair of electrode pads each comprising a gel portion:
 lead wires, wherein one end of each of the lead wires is electrically connected to the corresponding gel portion, and the other end of each of the lead wires extends to an outside of a package, and the lead wires and the pair of electrode pads are sealed in the package:
 a pair of nonconductive release liners each detachably stuck to the corresponding gel portion and each having a through hole opposed to the corresponding gel portion; and
 a connecting member comprising an electric connecting pattern having a predetermined electrical resistance, wherein the pair of gel portions, each of which is exposed from the corresponding through hole, are electrically connected to each other through the electric connecting pattern in a state where each of the pair of release liners are stuck to the corresponding gel portion, wherein the connecting member has a cut region by which the pair of gel portions are electrically disconnected to each other when the pair of electrode pads are stuck to a living body.

According to the present invention, the gel portions, which are exposed from the through holes of the release liners, are electrically connected to each other by the connecting member including the electric connecting pattern having a certain electrical resistance in a state where each of the nonconductive release liners is stuck to the corresponding gel portion of each of the pair of electrode pads. During storage, therefore, a conduction test can be performed in the package by causing a current to flow through the lead wires respectively connected to the electrode pads. The connecting member includes the cut region by which the pair of gel portions are electrically disconnected to each other when the pair of electrode pads are stuck to a living body. After the pair of electrode pads are used, the electrical connection is broken, that is, the pair of gel portions are electrically disconnected to each other. Even when the pair of electrode pads are housed through the release liners in the package while the gel portions of the pads are opposed to each other, consequently, a conduction state is not obtained, and hence it is possible to check that the electrode pads have been used. Also when, after the pair of electrode pads are used, the defibrillation pad is housed while the gel portions are connected and opposed to each other, the resistance is changed from that obtained before the pads are used, and therefore it is possible to check that the electrode pads have been used.

BRIEF DESCRIPTION OF DRAWINGS

FIG. 1 is an assembly perspective view showing a first embodiment of the defibrillation pad.

FIG. 2 is a plan view of the first embodiment of the defibrillation pad, as viewed from the side where release liners are stuck.

FIG. 3 is a plan view of a connecting member used in embodiments of the defibrillation pad.

FIG. 4 is a sectional view of a connecting portion in which electrode pads in the first embodiment of the defibrillation pad are connected to each other by the connecting member and a covering member, and which is in a stacked state.

FIG. 5 is a plan view showing a state where connecting portions of the electrode pads in the first embodiment of the defibrillation pad are separated from each other.

FIG. 6 is a plan view of a second embodiment of the defibrillation pad, as viewed from the side where release liners are stuck.

FIG. 7 is a front view showing a pair of electrode pads, which are stacked together and housed in a package in the second embodiment of the defibrillation pad.

FIG. 8 is a front view partially sectioned showing a pair of electrode pads, which are stacked together and housed in a package in a third embodiment of the defibrillation pad.

DESCRIPTION OF EMBODIMENTS

Hereinafter, exemplary embodiments of the invention will be described with reference to the accompanying drawings. In the figures, the identical components are denoted by the same reference numerals, and duplicated descriptions will be omitted. FIG. 1 is an assembly perspective view showing a first embodiment of the defibrillation pad, and FIG. 2 is a plan view as viewed from the side where release liners are stuck. A pair of electrode pads 10 which are identical to each other are disposed, and gel portions 12 each including an electrically conductive gel layer are disposed on the rear surface side of nonconductive sheets 11.

Pictures (not shown) indicating positions of the living body to which the electrode pads 10 are to be stuck are printed on the front surfaces of the nonconductive sheets 11.

In the vicinities of one edges of the electrode pads 10, 10, terminals 23, 23 which are electrically connected to one ends of lead wires 21, 22 are riveted by rivets or the like to the sides of the gel portions 12, 12, and electrically conductive with the gel portions 12, 12, respectively. The other ends of the lead wires 21, 22 are connected to a connector 24 which is used for obtaining electrical connection with a defibrillator (not shown). The connector 24 is previously connected to the defibrillator so that a voltage can be applied to the defibrillation pad at any time.

Nonconductive release liners 30A, 30B are detachably stuck to the gel portions 12, respectively. The release liners 30A, 30B have a rectangular plan-view shape which is approximately similar to the plan-view shape of the electrode pads 10. Tabs 31 which are projected to the outside are formed in portions which, in a state where the release liners 30A, 30B are stuck to the gel portions 12, are close to one edges on one end side where the terminal 23 are disposed. The tabs 31 are disposed in order to enable the release liners 30A, 30B to be easily picked by fingers or the like when the release liners are to be peeled off.

Through holes 32A, 32B having, for example, a substantially square plan-view shape are formed at positions of the release liners 30A, 30B which are in proximity to adjacent side edges of the pair of electrode pads 10, 10 in a state where the electrode pads 10, 10 are closely juxtaposed while the release liners 30A, 30B are stuck thereto, respectively.

The reference numeral 40 denotes a connecting member. As shown in FIG. 3, the connecting member 40 includes a strip-like flexible printed circuit board which, on one surface, includes an electric connecting pattern 41, and exposed portions 43, 43 that are electrically connected to both end portions of the electric connecting pattern, respectively. In the strip-like flexible printed circuit board, the electric connecting pattern 41 and the exposed portions 43, 43 are formed on one surface of a PET board or the like by a conductive carbon ink. The exposed portions 43, 43 are formed in the both end portions of the electric connecting pattern 41 so as to have a substantially square plan-view shape, and to be slightly larger than the through holes 32A, 32B which are disposed in the release liners 30A, 30B. The electric connecting pattern 41 is a resistance pattern which is thin in order to obtain a predetermined resistance. The electric connecting pattern 41 meanders in an S-shape in the vicinities of the exposed portions 43, 43, and is formed into a linear shape along the longitudinal direction of the connecting member 40 in the vicinity of the middle portion of the electric connecting pattern 41 in the longitudinal direction.

The resistance of the electric connecting pattern 41 is set in the following manner by adjusting the length and width of the resistance pattern. The transthoracic impedance of an adult is about 70 to 80 W. Therefore, the resistance is set between a value (the lower limit resistance RL of the electric connecting pattern) which is higher than the transthoracic impedance, and a value (the upper limit resistance RH of the electric connecting pattern) which is lower than the total resistance (the use limit resistance of the gel, about 5 to 10 kW) of the electrode pads 10, 10 that are dried until they become unsuitable for use. Preferably, the resistance is set between 350 W and 3.500 W in consideration of variations of the device impedance and the transthoracic impedance, the kind of the gel, and the like.

The portion where the electric connecting pattern 41 is formed is insulation-coated by a resist 44, and the exposed portions 43, 43 are not coated by a resist and are exposed. FIG. 3 is drawn under the assumption that the resist 44 is transparent. In the connecting member 40, in a state where the release liners 30A. 30B are stuck to the electrode pads 10, 10, the exposed portions 43, 43 are disposed while being directed toward the release liners 30A, 30B. In the connecting member 40, the distance between the exposed portions 43, 43 is determined so that the exposed portions 43, 43 are located in the through holes 32A, 32B, respectively. Therefore, the connecting member 40 connects the release liner 30A and the release liner 30B to each other, and the electric connecting pattern 41 electrically connects together the gel portions 12, 12 which are exposed from the through holes 32A. 32B.

The connecting member 40 has a cut region 45 in which the electric connecting pattern 41 is broken when the electrode pads 10, 10 are to be stuck to the living body. The cut region 45 is disposed in the vicinity of the middle portion of the connecting member 40 in the longitudinal direction, and configured so as to be breakable more easily than the other region. In the cut region 45 in the embodiment, notches 46 are formed in both end portions of the connecting member 40 in the width direction. As each of the notches 46, a single V-like notch is disposed in one end. Alternatively, a plurality of V-like notches which are laterally arranged in one end may be formed as the notch. The notches 46 are not limited to have a V-like shape, but may be, for example, simple cuts. As described above, the electric connecting pattern 41 in the vicinity of the middle portion is a single linear pattern. Therefore, the region where the V-like notches or the cuts are formed is configured so as to be breakable more easily than the other region.

The reference numeral 50 (see FIGS. 1 and 2) denotes a covering member which covers the connecting member 40. The covering member 50 has a sheet-like shape, and a rectangular plan-view shape. The edges of the covering member are chamfered. In order to cover the whole surface of the connecting member 40, the covering member 50 is formed slightly larger than the connecting member 40. In the covering member 50, a resin is used as the base material, and one surface is formed as an adhesive surface 51.

A thin long hole 52 is opened in a middle portion of the covering member 50. The long hole 52 is formed so that the longitudinal length is slightly larger than the width dimension of the connecting member 40. Perforated portions 53 are linearly formed so as to extend from the both end portions of the long hole 52 toward the outside, respectively. When the adhesive surface 51 of the covering member 50 is coveringly stuck to the connecting member 40 and the release liners 30A, 30B in the peripheral vicinity thereof, the connecting member 40 can be secured to the release liners 30A, 30B.

FIG. 2 is a plan view of the defibrillation pad in which the pair of electrode pads 10, 10 are connected to each other by the connecting member 40, and the connecting member 40 is covered by the covering member 50. Specifically, the connecting member 40 is disposed so that edge portions of electrode pads 10, 10 are butted against each other, the release liners 30A, 30B are stuck to the gel portions 12, 12, the exposed portions 43, 43 are placed on the release liners and located in the through holes 32A, 32B, and the notches 46, 46 are placed along the butted edge portions of the electrode pads 10, 10. Moreover, the covering member 50 is coveringly stuck to the connecting member 40 so that the longitudinal direction of the long hole 52 coincides with the notches 46, 46 in the direction along the edge portions, and the portion of the connecting member 40 in the width direction is within the range of the long hole 52 in the longitudinal direction. In this state, the defibrillation pad is folded so that the surface (in FIG. 2, the rear side of the sheet) on which the pictures are drawn is on the front side, and the electrode pads 10, 10 are stacked together.

When the defibrillation pad is folded as described above, the connecting member 40 and the covering member 50 are smoothly bent in the bent portion of the defibrillation pad. FIG. 4 is a sectional view of the portion where the connecting member 40 and the covering member 50 are connected to each other in the stacked electrode pads 10, 10. The figure illustrates only the portion where the connecting member 40 is shown in section, and illustration of the other portion is omitted.

As seen from FIG. 4, in the bent portion of the connecting member 40, a space is formed because of the long hole 52 (refer also to FIGS. 1 and 2) of the covering member 50 and the thickness of the covering member 50. Therefore, the connecting member 40 can be bent without effort, and the electrode pads 10, 10 can be stacked together without causing the electric connecting pattern 41 to be broken.

As a result of the folding, the tabs 31, 31 of the release liners 30A, 30B are placed in the inner side, and therefore the plan-view shape of the whole stacked electrode pads 10, 10 is a square shape. The folded defibrillation pad is housed in a gas and liquid impermeable package which is not shown. At this time, the lead wires 21, 22 extend from the interior of the package to the external connector 24. Then, the package housing the stacked electrode pads 10, 10 and parts of the lead wires 21, 22 is hermetically sealed.

In the package, a state is formed in which the gel portions 12, 12 that are exposed respectively from the through holes 32A, 32B are electrically connected to each other by the electric connecting pattern 41 of the connecting member 40. Therefore, a conduction test can be performed by connecting an apparatus having a function of a conduction test, such as a defibrillator, to the connector 24.

When the defibrillation pad is to be used, for example, a predetermined portion of the package is torn off, the stacked electrode pads 10, 10 which are housed in the package are taken out, and the defibrillation pad is unfolded, with the result that the state of FIG. 2 is obtained. When the state of FIG. 2 is turned upside down, the pictures printed on the surfaces of the electrode pads 10, 10 appear. This is convenient because positions of the living body to which the electrode pads 10, 10 are to be stuck can be easily known. Next, the electrode pads 10, 10 are held by the right and left hands, respectively, and then pulled in the direction along which they are separated from each other, whereby the covering member 50 is cut off at the perforated portions 53, and the portion between the notches 46, 46 of the cut region 45 in the connecting member 40 is ruptured. Therefore, the electrode pads 10, 10 can be separated from each other as shown in FIG. 5. Thereafter, the release liners 30A, 30B are peeled off, and the electrode pads 10, 10 are stuck to the predetermined positions of the living body. As a result, the defibrillator can apply a voltage to the living body.

After the use, the electrode pads 10, 10 are already separated from each other, and therefore the electric connecting pattern 41 of the connecting member 40 is broken. Even when the release liners 30A, 30B to which the connecting member 40 and the covering member 50 remain to be stuck are bonded to the gel portions 12, and then the resulting members are housed in the package in a similar manner as that before the use, therefore, electrical conduction is not obtained between the electrode pads 10, 10, and, when a conduction test is performed, it is possible to easily detect that the electrode pads 10, 10 have been used. Also in the case where the gel portions 12, 12 of the electrode pads 10, 10 are directly bonded together and electrical conduction is obtained between the electrode pads 10, 10, it is possible to easily detect that the electrode pads 10, 10 have been used. Next, detection of such an abnormal state will be described.

In the embodiment, a conduction test is performed by the defibrillator in the following manner. During storage (waiting), a conduction test is performed automatically and periodically on the electrode pads 10, 10 which has been hermetically sealed as described above and connected to the defibrillator. In the conduction test, the resistance of the defibrillation pad is detected by the defibrillator, and the detected resistance of the defibrillation pad is compared with the lower limit resistance RL and upper limit resistance RH of the electric connecting pattern, thereby detecting whether an abnormality occurs or not. In the conduction test performed during storage, breakage or short-circuit of the energization system, the dry condition of the gel, and the used/unused status of the electrode pads are detected. In the conduction test performed when the electrode pads are stuck to the living body (during use), the attachment state of the electrode pads is detected. During both storage and use, if abnormality occurs, the defibrillator notifies of this.

Table 1 shows states of the defibrillation pad with respect to comparisons among the detected resistance R of the defibrillation pad, and the lower limit resistance RL and upper limit resistance RH of the electric connecting pattern. Firstly, the state during storage (waiting) will be described. In the case where the resistance R of the defibrillation pad is lower than the lower limit resistance RL of the electric connecting pattern (R<RL), it is possible to detect that the defibrillation pad has been used and the gel portions are directly bonded together. In the case where R is higher than the upper limit resistance RH of the electric connecting pattern (R>RH), it is possible to detect, for example, that, in the defibrillation pad, the gel is in the dry condition, the electrode pads have been used and remain separated from each other, or line breakage occurs. In the case where R is between RL and RH (RL≤R≤RH), it is possible to detect that the defibrillation pad is normal. Next, the state during use will be described. In the case where R is higher than RH (R>RH), it is possible to detect that the defibrillation pad has not yet been attached or an attachment failure occurs. In the case where R is lower than RL, it is possible to detect that the defibrillation pad is normally attached. In the case where R is between RL and RH (RL≤R≤RH), it is possible to detect that an attachment failure occurs.

TABLE 1

| Resistance of defibrillation pad R | During storage (waiting) | During use |
| --- | --- | --- |
| R > RH | gel dry/used (separated)/breakage | not yet attached/attachment failure |
| RL ≤ R ≤ RH | Normal | attachment failure |
| R < RL | used (directly bonded) | normally attached |

In the conventional electrode pads disclosed in above-described Configuration example 1 and JP5113183B2, in the case where, after use, the electrode pads are housed in a package while the gel surfaces are opposed to each other, electrical conduction is obtained in a similar manner as electrode pads which are normally stored, and therefore it is impossible to detect the state where the pads have been used. In the defibrillation pad of the embodiment, in the case where the defibrillation pad is normally stored as described above, by contrast, R is between RL and RH, and, in the case where, after use, the gel surfaces are directly bonded to each other, R<RL is obtained with the result that this case can be distinguished from the case where the defibrillation pad is normally stored.

FIG. 6 shows a second embodiment of the defibrillation pad. The second embodiment is configured in an almost identical manner as the first embodiment. The second embodiment is different from the first embodiment in that the second embodiment includes a release liner connecting member 60.

The release liner connecting member 60 has a sheet-like shape, and a rectangular plan-view shape which is vertically elongated. The edges of the member are chamfered. Similarly in the covering member 50, in the release liner connecting member 60, a resin is used as the base material, and one surface is formed as an adhesive surface 61 (the rear side in FIG. 6). The release liner connecting member 60 is configured so as to have a higher resistance to cutting than a combination of the covering member 50 and the connecting member 40. In other words, the covering member 50 includes the long hole 52 and the perforated portions 53, the connecting member 40 includes the notches 46, and, even when the both members are combined with each other, the resistance to cutting is weaker than that of the release liner connecting member 60. The release liner connecting member 60 may be formed of a material having a higher resistance to cutting than the covering member 50. Alternatively, the resistance to cutting may be made higher than that of the covering member 50 by increasing the thickness of the release liner connecting member 60. As the adhesive agent of the adhesive surface 61, an adhesive agent may be used which has a higher adhesive strength than that of the adhesive surface 51 of the covering member 50.

The release liner connecting member 60 may be used after the release liners 30A, 30B are connected to each other by the covering member 50. In one release liner 30A (or 30B), namely, the release liner connecting member 60 is stuck to an edge portion of the one release liner 30A (or 30B) as shown in FIG. 6, the edge portion being opposite to that to which the covering member 50 is stuck.

Similarly with the first embodiment, the defibrillation pad is folded so that the surface on which the pictures are drawn is on the front side, and the electrode pads 10, 10 are stacked together. At this time, the adhesive surface 61 in the region where the release liner connecting member 60 protrudes from the release liner 30A is bonded to the release liner 30B.

The release liner connecting member 60 is bonded to the release liners 30A, 30B, and the stacked electrode pads 10, 10 are housed in a package similarly with the first embodiment. When the electrode pads 10, 10 are housed in the package while the pads are formed into a tubular shape as shown in FIG. 7, the connecting member 40 is more hardly breakable. This is similarly applicable also to the first embodiment.

When the defibrillation pad is to be used, the stacked electrode pads 10, 10 are taken out from the package, and the electrode pads 10, 10 are separated from each other, usually by the hands. At this time, portions of the covering member 50 and the connecting member 40 are torn off because the release liner connecting member 60 is configured to have a higher resistance to cutting than the combination of the covering member 50 and the connecting member 40.

According to the second embodiment, when to be used, namely, the portions of the covering member 50 and the connecting member 40 can be surely torn off, and the electric connecting pattern 41 of the connecting member 40 is broken. At this time, the release liner connecting member 60 is bonded to the release liners 30A, 30B. When one of the tabs 31 is hand-picked and one release liner 30A (or 30B) is peeled off the gel portion 12, therefore, also the other release liner 30B (or 30A) which is joined to the peeled release liner through the release liner connecting member 60 can be peeled off the corresponding gel portion 12. This is convenient.

Also in the second embodiment, when a conduction test is performed on the electrode pads 10, 10 during storage in a manner similar to the first embodiment, the state of the electrode pads 10, 10 can be detected as shown in Table 1 above. In addition to whether the electrode pads 10, 10 are abnormal or not, it is possible to detect that, even when, after use, the release liners 30A, 30B to which the connecting member 40 and the covering member 50 remain to be stuck are bonded to the gel portions 12, and then the resulting members are returned to the original state in a similar manner as that before the use, the electrode pads 10, 10 have been used. Also when the gel portions 12, 12 are directly bonded together and electrical conduction is obtained between the electrode pads 10, 10, it is possible to easily detect that the electrode pads 10, 10 have been used.

According to the second embodiment, in addition to the effect similar to that of the first embodiment, the following effect can be achieved. The release liner connecting member 60 is configured so as to have a higher resistance to cutting than the combination of the covering member 50 and the connecting member 40. When the electrode pads 10, 10 are to be stuck to the living body, therefore, portions of the covering member 50 and the connecting member 40 can be surely cut off.

FIG. 8 shows a third embodiment of the defibrillation pad. The third embodiment is configured in an almost identical manner as the second embodiment. The third embodiment is different from the second embodiment in following (1) to (3):

(1) the defibrillation pad is folded so that the electrode pads 10, 10 are stacked together while setting the surfaces of the release liners 30A, 30B as the front side;

(2) since the surfaces of the release liners 30A, 30B are in the front side, the release liner connecting member 60 is bonded from the front side, and the shape, material, and the like of the release liner connecting member 60 are identical with those of the second embodiment; and (3) when the electrode pads 10, 10 are stacked together, the connecting member 40 and the covering member 50 are on the outer side with respect to the electrode pads 10, 10, and therefore the connecting member 40 and the covering member 50 are stuck in a state where the electrode pads 10, 10 are separated from each other.

In the first and second embodiments, the breakage of the electric connecting pattern 41 which may be possibly caused by bending the connecting member 40 is prevented from occurring by the long hole 52 of the covering member 50. In the third embodiment, as described above, the defibrillation pad is folded so that the electrode pads 10, 10 are stacked together while setting the surfaces of the release liners 30A, 30B as the front side. Therefore, the connecting member 40 and the covering member 50 are on the outer side with respect to the electrode pads 10, 10. When the electrode pads 10, 10 are stacked together, the connecting member 40 and the covering member 50 are pulled, and there arises a possibility that the electric connecting pattern 41 is broken. In order to prevent the breakage from occurring, the electrode pads 10, 10 are separated from each other by a predetermined distance d, and then the connecting member 40 and the covering member 50 are stuck.

When the defibrillation pad is folded so that the electrode pads 10, 10 are stacked together, the distance between the edges of the electrode pads 10, 10 in the bent portion is twice the total thickness of the nonconductive sheet 11 and the release liner 30A. Therefore, the electrode pads 10, 10 must be separated from each other by at least the distance. In the case where the total thickness of the nonconductive sheet 11 and the release liner 30A is 1 mm, for example, the electrode pads 10, 10 must be separated from each other by at least two times the thickness, i.e., 2 mm. When the separation distance is 2 mm, however, the connecting member 40 is bent at a right angle in edge corner portions of the electrode pads 10, 10 in the bent portion, and hence there is a possibility that the electric connecting pattern 41 is broken. As shown in FIG. 8, therefore, the connecting member 40 and the covering member 50 are bent into a semicircular shape. Since the diameter of the semicircle is 2 mm, the semicircumference is about 3 mm. Therefore, the distance d between the electrode pads 10, 10 may be set to 3 mm. According to the configuration, the connecting member 40 is smoothly bent, and not sharply bent at the edges of the electrode pads 10, 10. Consequently, the electric connecting pattern 41 can be prevented from being bent and broken.

As described in the description of the second embodiment, the release liner connecting member 60 may be used before the electrode pads 10, 10 are stacked together, and after the release liners 30A, 30B are connected to each other by the covering member 50. As described below, alternatively, the release liner connecting member 60 may be used after the electrode pads 10, 10 are stacked together.

The electrode pads 10, 10 are bent in the portion where the edge portions of the electrode pads 10, 10 are opposed to each other, in such a manner that the surfaces on which the pictures are drawn are on the rear side, and folded so that the electrode pads 10, 10 are stacked together. Next, the release liner connecting member 60 is bonded to the release liners 30A, 30B in the edge portions which are opposite to those in the bent portion.

Also in the third embodiment, similarly with the second embodiment, the conduction test can be performed in the state where the defibrillation pad is housed in the package. As shown in Table 1, in addition to whether the electrode pads 10, 10 are abnormal or not, it is possible to detect that, even when, after use, the release liners 30A, 30B to which the connecting member 40 and the covering member 50 remain to be stuck are bonded to the gel portions 12, and then the resulting members are returned to the original state in a similar manner as that before the use, the electrode pads 10, 10 have been used. Also when the gel portions 12, 12 are directly bonded together and electrical conduction is obtained between the electrode pads 10, 10, it is possible to easily detect that the electrode pads 10, 10 have been used.

According to the third embodiment, in addition to the effects similar to those of the second embodiment, the following effect is achieved. Since the release liner connecting member 60 is on the front side, the release liner connecting member 60 can be easily attached to the electrode pads, and therefore the productivity is high.

This application is based on Japanese Patent Application No. 2014-248584 filed on Dec. 9, 2014, the entire content of which is incorporated herein by reference.

The invention claimed is:

1. A defibrillation pad for a defibrillator, comprising:
a pair of electrode pads each comprising a gel portion; connected to the corresponding gel portion;
a pair of nonconductive release liners each separately and detachably stuck to the corresponding gel portion and each having a through hole opposed to the corresponding gel portion; and
a connecting member comprising an electric connecting pattern having a predetermined electrical resistance, wherein the connecting member is configured to connect the pair of release liners such that the pair of gel portions, each of which is exposed from the corresponding through hole, are electrically connected to each other through the electric connecting pattern in a state where each of the pair of release liners are stuck to the corresponding gel portion,
wherein the connecting member has a cut region in which the electric connecting pattern is breakable to electrically disconnect the pair of gel portions from each other and to separate the pair of electrode pads from each other when the pair of electrode pads are to be stuck to a living body.

2. The defibrillation pad of claim 1, wherein the electrical resistance is set based on a transthoracic impedance of the living body and a use limit resistance of the gel portions.

3. The defibrillation pad of claim 1,
wherein the connecting member is a strip-like flexible printed circuit board and comprises:
the electric connecting pattern, which is formed in a middle portion of the connecting member in a longitudinal direction of the connecting member; and
a pair of exposed portions which are exposed to the outside and each of which is electrically connected to a corresponding one of both ends of the electric connecting pattern, and is formed in a corresponding one of end portions of the connecting member in the longitudinal direction of the connecting member, and
wherein each of the pair of exposed portions is electrically connected to the corresponding gel portion exposed from the through hole.

4. The defibrillation pad of claim 1, wherein the cut region is configured to be cut more easily than any other portion of the connecting member.

5. The defibrillation pad of claim 4, wherein a notch is formed in the cut region of the connecting member.

6. The defibrillation pad of claim 1, further comprising
a sheet-like covering member which is stuck to the connecting member and the pair of release liners in a vicinity of the connecting member to cover the connecting member.

7. The defibrillation pad of claim 6,
wherein the connecting member has a strip-like shape elongating in an arrangement direction of the gel portions,
wherein in the cut region, a notch is formed in each of both end portions of the connecting member in a width direction of the connecting member,
wherein the covering member has a linear long hole having a predetermined width in a vicinity of a middle portion thereof, and a longitudinal length of the hole is larger than a width of the strip-like connecting member,
wherein in a state where first edge portions of the pair of electrode pads are opposed to each other, the connecting member is disposed such that the notches are arranged in a direction along the first edge portions, and
wherein the covering member is stuck to the connecting member and the release liners in a vicinity of the connecting member, such that a longitudinal direction of the long hole is equal to the direction along the first edge portions of the pair of electrode pads opposed to each other, the long hole is overlapped with the notches and a width of the connecting member is within the long hole.

8. The defibrillation pad of claim 7, further comprising:
a release liner connecting member configured to connect second edge portions of the pair of release liners to each other, wherein the second edge portions are opposite to the first edge portions of the release liners, which are connected to each other by the covering member.

9. The defibrillation pad of claim 8, wherein the release liner connecting member has a higher resistance to cutting than a combination of the covering member and the connecting member.

10. The defibrillation pad of claim 1, wherein the connecting member is bendable in a U shape in a state in which the connecting member connects the release liners to each other such that the connecting member is sandwiched between the pair of release liners and such that a bent portion of the connecting member is detached from the release liners.

11. The defibrillation pad of claim 1, wherein, in a state in which the electrode pads are arrange side by side with the release liners being stuck to the respective electrode pads, the through holes of the release liners are provided closer to adjacent side edges of the electrode pads than other side edges of the electrode pads.

12. A defibrillation pad for a defibrillator, comprising:
a pair of electrode pads each comprising a gel portion;
lead wires, wherein one end of each of the lead wires is electrically connected to the corresponding gel portion;
a pair of nonconductive release liners each detachably stuck to the corresponding gel portion and each having a through hole opposed to the corresponding gel portion;
a connecting member comprising an electric connecting pattern having a predetermined electrical resistance, wherein the pair of gel portions, each of which is exposed from the corresponding through hole, are electrically connected to each other through the electric connecting pattern in a state where each of the pair of release liners are stuck to the corresponding gel portion; and
a sheet-like covering member which is stuck to the connecting member and the pair of release liners in a vicinity of the connecting member to cover the connecting member,
wherein the connecting member has a cut region by which the pair of gel portions are electrically disconnected to each other when the pair of electrode pads are stuck to a living body,
wherein the connecting member has a strip-like shape elongating in an arrangement direction of the gel portions,
wherein in the cut region, a notch is formed in each of both end portions of the connecting member in a width direction of the connecting member,
wherein the covering member has a linear long hole having a predetermined width in a vicinity of a middle portion thereof, and a longitudinal length of the hole is larger than a width of the strip-like connecting member, wherein in a state where first edge portions of the pair of electrode pads are opposed to each other, the connecting member is disposed such that the notches are arranged in a direction along the first edge portions, and wherein the covering member is stuck to the connecting member and the release liners in a vicinity of the connecting member, such that a longitudinal direction of the long hole is equal to the direction along the first edge portions of the pair of electrode pads opposed to each other, the long hole is overlapped with the notches and a width of the connecting member is within the long hole.

13. The defibrillation pad of claim 12, further comprising: a release liner connecting member configured to connect second edge portions of the pair of release liners to each other, wherein the second edge portions are opposite to the first edge portions of the release liners, which are connected to each other by the covering member.

14. The defibrillation pad of claim 13, wherein the release liner connecting member has a higher resistance to cutting than a combination of the covering member and the connecting member.

* * * * *